United States Patent [19]

Wu

[11] Patent Number: 5,744,677
[45] Date of Patent: Apr. 28, 1998

[54] ETHYLENE OLIGOMERIZATION

[75] Inventor: Feng-Jung Wu, Baton Rouge, La.

[73] Assignee: Amoco Corporation, Chicago, Ill.

[21] Appl. No.: 914,489

[22] Filed: Jul. 14, 1992

Related U.S. Application Data

[63] Continuation of Ser. No. 777,137, Oct. 16, 1991, abandoned.

[51] Int. Cl.$^6$ .................................................. C07C 2/36
[52] U.S. Cl. .................... 585/512; 585/511; 585/520; 502/117; 502/305
[58] Field of Search ........................ 585/511, 512, 585/520, 527, 530, 532; 502/305

[56] References Cited

U.S. PATENT DOCUMENTS

| | | | |
|---|---|---|---|
| 3,726,939 | 4/1973 | Zuech | 260/683.15 D |
| 4,668,838 | 5/1987 | Briggs | 585/513 |
| 4,777,315 | 10/1988 | Levine et al. | 585/512 |
| 4,849,487 | 7/1989 | Kaminski et al. | 526/160 |
| 4,853,356 | 8/1989 | Briggs | 502/117 |
| 4,933,403 | 6/1990 | Kaminski et al. | 526/160 |

*Primary Examiner*—Ponnathapura Achutamurthy
*Attorney, Agent, or Firm*—James R. Henes; Stephen L. Hensley

[57] ABSTRACT

Alpha-olefins enriched in 1-hexene are prepared by oligomerizing ethylene in the presence of a catalyst comprising (a) a chromium complex containing a coordinating polydentate ligand and, (b) an aluminoxane, in an organic solvent.

16 Claims, No Drawings

ETHYLENE OLIGOMERIZATION

This application is a continuation of application Ser. No. 07/777,137, filed Oct. 16, 1991, now abandoned.

This invention relates generally to the oligomerization/trimerization of ethylene and more specifically to the preparation of high quality linear α-olefins from ethylene using a catalyst which includes an aluminoxane and a chromium complex containing a coordinating polydentate ligand, such as a 1,4,7-triazacyclononane derivative.

The preparation of linear, $C_4$ to $C_{30}$ α-olefin mixtures by ethylene chain growth process using triethylaluminum followed by ethylene displacement is well known. The olefin type produced is mainly α-olefins, i.e. R—CH=CH$_2$, where R is an aliphatic hydrocarbon group, but the product also contains lesser amounts of internal olefins, i.e. R—CH=CH—R, where R is an aliphatic hydrocarbon group, and vinylidene olefins, i.e.

where R and R' are aliphatic hydrocarbon groups. When practiced to produce olefin mixtures containing up to 12 carbon atoms, the mixtures are predominantly, i.e. about 80 mole percent or more α-olefins. However when practiced to produce higher olefins, e.g. containing 14 or more carbon atoms, the amount of internal olefins, and especially vinylidene olefins, increases sharply such that in the $C_{16-18}$ olefin range the olefin mixture will contain about 20 to 55 mole percent vinylidene olefins and 5 to 20 mole percent internal olefins. In some uses the internal and vinylidene olefin content of the olefin mixtures is not detrimental. However, it is known that vinylidene olefins are readily sulfonated but the detergency and wetting performance of the derived sulfonates are inferior to those of sulfonates based on the corresponding linear α-olefins. Similar reservations apply to sulfonates of internal olefins. Also, as is well known, the reaction of α-olefins with HBr can lead to the 1-bromo or to the 2-bromo derivative depending on the reaction conditions. In the detergent industry, the 1-bromo derivatives are of more interest as they provide a route to dialkylamines and hence to amine oxides and quaternary amines. It is reported that any internal olefins present (which in principle are more reactive than α-olefins) will react to form internal bromides. Similarly, vinylidene olefins would rapidly add HBr. Hence, an impure α-olefin would lead ultimately to a tertiary amine containing a wide range of impurities. Thus, with products obtained by ethylene chain growth, a need often exists to separate internal and vinylidene olefins from mixtures containing vinyl, vinylidene and internal olefins which mixtures cannot be readily separated by distillation.

Another problem with the chain growth process is that the commercial demand for 1-hexene often exceeds the amount which is obtainable from even the most favorable chain growth product distribution.

An ethylene oligomerization process has now been found which produces high quality α-olefins which are unexpectedly enriched in 1-hexene.

In accordance with this invention there is provided a process for preparing α-olefins, said process comprising oligomerizing ethylene in the presence of a catalyst comprising (a) a chromium complex containing a coordinating polydentate ligand and (b) an aluminoxane, in an organic solvent.

Also provided is a catalyst comprising (a) a chromium complex containing a coordinating polydentate ligand and (b) an aluminoxane.

Aluminoxanes for use in the process of the invention can be prepared as known in the art by reacting water or water containing materials with trialkylaluminum compounds in proportions of from about 0.5 to 1.2 equivalents of water and, preferably, 0.8 to 1.0 equivalents of water per equivalent of trialkylaluminum. For example, Manyik et al U.S. Pat. No. 3,300,458 prepare alkylaluminoxane by passing a hydrocarbon solvent through water to form a wet hydrocarbon solvent and mixing the wet hydrocarbon solvent with an alkyl aluminum/hydrocarbon solvent mixture in a conduit.

Schoenthal et al. U.S. Pat. No. 4,730,071 show the preparation of methylaluminoxane by dispersing water in toluene using an ultrasonic bath and then adding a toluene solution of trimethyl aluminum to the dispersion. Schoenthal et al U.S. Pat. No. 4,730,072 is similar except it uses a high speed, high shear-inducing impeller to form the water dispersion.

Edward et al. U.S. Pat. No. 4,772,736 describe an aluminoxane process in which water is introduced below the surface of a solution of hydrocarbyl aluminum adjacent to a stirrer which serves to immediately disperse the water in the hydrocarbon solution.

The preparation of alkyl aluminoxanes from $R_2AlOLi$ formed by reacting $AlR_3$ and anhydrous lithium hydroxide, and $R_2AlCl$ has been reported in the literature, for example, Ueyama et al., Inorganic Chemistry, 12, No. 10, 2218 (1973) and Aoyazi et al., Inorganic chemistry, 12, No. 11, 2702 (1973).

Sinn et al. U.S. Pat. No. 4,404,344 prepare methylaluminoxane by adding trimethyl aluminum to a slurry of $CuSO_4 \cdot 5H_2O$ in toluene. Introducing water as a metal hydrate controls its reactivity with the trimethyl aluminum. Kaminsky et al. U.S. Pat. No. 4,544,762 is similar except it uses an aluminum sulfate salt hydrate to supply the water. Likewise, Welborn et al. U.S. Pat. No. 4,665,208 describe the use of other metal salt hydrates such as $FeSO_4 \cdot 7H_2O$ as a water source in preparing aluminoxane.

Hydrocarbylaluminoxanes may exist in the form of linear or cyclic polymers with the simplest compounds being a tetraalkylaluminoxane such as tetraethylaluminoxane, $(C_2H_5)_2AlOAl(C_2H_5)_2$. The compounds preferred for use are prepared from hydrocarbylaluminum compounds in which the alkyl groups contain an even number of carbon atoms, e.g. 2, 4, 6, 8, 10 etc. Using methylaluminoxane can result in α-olefin mixtures which contain odd carbon number α-olefin impurities and tends to produce products having longer chain lengths. Preferred aluminoxanes are prepared from trialkyl aluminum compounds such as triethyl aluminum, triisobutyl aluminum, tri-n-hexyl aluminum, trioctyl aluminum and the like. Of these, the more preferred are the compounds having $C_6$ or higher alkyl groups which have better solubility in the hydrocarbon solvent reaction medium. The aluminoxanes used to form the catalyst are preferably contained in organic solvents in concentrations of from about 0.3 to 30 weight percent of total solvent plus aluminoxane.

A trialkylaluminum compound can also be included in the catalyst (0.1 to 1.0 mole per mole of aluminoxane).

The chromium complexes which, upon mixing with an aluminoxane, catalyze ethylene oligomerization and trimerization in accordance with the process of the invention can be represented by the formula: $LCrX_3$ or $LCrX_2$, where L is a coordinating polydentate ligand and X represents anions which can be the same or different.

By a coordinating ligand is meant that the ligand sterically encumbers the chromium atom to such an extent that the rate of chain propagation is decreased so that oligomerization rather than polymerization occurs. For example, ligands which occupy three neighboring coordination sites about an octahedral chromium atom. Examples of such preferred coordinating polydentate ligands are cyclic polyamine ligands which are represented by the abbreviation: A—NR—B, where A is an integer of 9 to 18, B is an integer of 3 to 6, and R is a $C_1$ to $C_{10}$ alkyl group such as a methyl, ethyl, propyl, butyl, pentyl, hexyl or higher alkyl group or a $C_6$ to $C_{20}$ aromatic group such as benzyl. The abbreviations, such as 9-NR-3, 10-NR-3, 12-NR-4 and the like, used for the amine ligands correspond to those used for crown ethers because they are their nitrogen analogues. For example, 9-NR-3 denotes a nine membered ring with 3 nitrogens. The most preferred coordinating polydentate ligands are facially coordinating tridentate ligands such as 9-NMe-3. Such sterically demanding ligands permit both ethylene oligomerization and trimerization while inhibiting ethylene polymerization. Other suitable facially coordinating tridentate ligands include poly(pyrazolyl) borates of the type: $RB(P_z)_3$ anions, where R is as defined above and $P_z$ is pyrazole or a substituted pyrazole such as 3,5-dimethyl pyrazole (see P. Trofimenko, Prog. Inorg. Chem, 1986, 34, 115–210. By polydentate is meant that the ligand contains multiple donor atoms for coordination with chromium.

Examples of suitable anions, X, include, but are not limited to, halides ($Cl^-$, $Br^-$, $I^-$, $F^-$), alkoxides ($OR^-$), carboxylates ($O_2CR^-$), $Oxo(O^{-2})$ and the like. These anions are initially the anion portion of the chromium compounds used to make the complex. The chromium in the compounds is initially in the oxidation state of 0 to VI and is preferably in the oxidation state of II, III or IV. Suitable chromium compounds are those which will provide the complex with active catalytic species for the oligomerization/trimerization reaction under the reaction conditions. For example: those which provide chromium complexes such as (9-NMe-3)$CrCl_3$, $HB(3,5-Me_2P)_3CrCl_3$, $[(14-NH-4)CrCl_2]Cl$ (or oxo-bridged dimer such as $[LCrCl_2]_2O$, where L is a tetradentate ligand), (9-NMe-3)$Cr(OR)_3$, (9-NMe-3)$Cr(O_2CR)_3$, (9-NMe-3)$CrO_3$, and the like.

Preferred ligands for complexing with the chromium compounds are the alkyl substituted 1,4,7-triazacyclononanes. For example, 1,4,7-trialkyl 1,4,7-triazanonanes which have the structure:

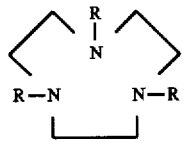

where each R can be the same or different $C_1$ to $C_{10}$ alkyl or $C_6$ to $C_{20}$ aromatic groups. An especially preferred ligand is 1,4,7-trimethyl-1,4,7-triazanonane. This ligand is commercially available.

The chromium complexes can be prepared according to procedures set forth in the literature. For example (9-NMe-3)$CrCl_3$, where Me is methyl, as per K. Wieghart et al., Inorg. Chem. 1982, 21, 3086 and (9-NMe-3)$CrBr_3$ as per P. Chaudhuri et al., Inorg. Chem. 1987, 26, 3302.

The chromium complex and aluminoxane are combined in proportions to provide Al/Cr molar ratios of from about 1:1 to 10,000 to 1 and, preferably, from about 5:1 to 500 to 1. For longer catalyst life, the catalyst components are combined in situ under ethylene pressure just prior to use in the oligomerization/trimerization reaction. Amounts of about 0.001 mmoles or more of chromium catalyst are effective to catalyze the reaction.

The reaction is carried out in an inert solvent. Any inert solvent can be used. The preferred solvents are aliphatic and aromatic hydrocarbons and halogenated hydrocarbons such as, for example, toluene, xylene, ethylbenzene, cumene, mesitylene, heptane, cyclohexane, methylcyclohexane, 1-hexene, 1-octene, chlorobenzene, dichlorobenzene, and the like. The amount of solvent is not particularly critical and generally ranges from about 50 to 99 wt. percent of the initial reaction mixture.

Reaction temperatures and pressures effect the chain length of the product and are selected to optimize the amount of the desired products. Higher temperatures provide lower carbon number products and higher ethylene pressures favor the production of longer chain length products including some polyethylene. In general, reaction temperatures can range from about 35° to 200° C. and, preferably, 95° to 150° C. Ethylene pressures can range from atmospheric to 3000 psig and, preferably from about 100–1500 psig.

The process produces chain growth products which are a Schulz-Flory distribution of $C_4$–$C_{30}$ α-olefins except that 1-hexene is selectively enriched which provides an economically attractive means of producing this α-olefin which is a widely used comonomer in linear low density polyethylene production. The process has the further advantage of producing α-olefin products without the formation of significant amounts of vinylidenes or polyethylene which tends to deactivate the catalyst and cause other operational problems.

Besides oligomerizing ethylene, co-oligomers of ethylene with minor amounts of other α-olefins such as propylene or butene-1 can also be prepared.

The invention is further illustrated by, but is not intended to be limited, to the following examples.

All operations involving the use of catalyst components were conducted under an inert atmosphere. Heptane, chlorobenzene, and toluene were freshly distilled under nitrogen from calcium hydride, phosphorus pentoxide, and sodium benzophenone ketyl, respectively. Triisobutylaluminum, trihexylaluminum and methylaluminoxane were commercial products of Ethyl Corporation and were used as received. 1,4,7-trimethyl-1,4,7-triazacyclononane (9-NMe-3), 1–4,7-triazacyclononane (9-NH-3), and 1,4,7-trithiacyclononane (9-S-3) were purchased from Aldrich and used as received. (9-NMe-3)$CrCl_3$, (9-NMe-3)$CrBr_3$, (9-NH-3)Cr(CO)$_3$, and $CrCl_3 \bullet 3$ Pyridine were prepared according to literature procedures. Ethylene is polymer grade from Matheson and was used without further purification.

PREPARATION OF N-HEXYLALUMINOXANE, NHAO

The reaction was carried out in an 1L three-necked round-bottom Morton flask equipped with a mechanical stirrer, a thermometer, and a rubber septum. To this flask containing a solution of trihexylaluminum (59.3 g, 0.200 mol) in toluene (129 g) with vigorous stirring, was added distilled water (3.10 ml, $H_2O$/Al molar ratio=0.86) using a syringe pump over a period of 45 minutes. The temperature was maintained at about 10°–15° C. by applying an ice bath. After water addition was complete, the solution was stirred at 50° C. for one additional hour and then allowed to air cool slowly. Since there was little or no insoluble material formed, a quantitative yield is assumed and Al wt percent is calculated to be 2.87% which agrees well with analysis. The solution was transferred and stored under inert atmosphere for subsequent reactions. The NHAO solution thus obtained remained active after up to 6 months of its preparation. The isobutylaluminoxane solutions (IBAO) were prepared analogously except in n-heptane instead of in toluene.

ETHYLENE OLIGOMERIZATION (EXAMPLES 1–15 AND COMPARISONS 1–4)

All reactions in Table I, unless otherwise noted, were carried out using the following exemplary procedures in which the specific process parameters and results described are those of Example 4.

Into a 300 ml Parr reactor equipped with a stirring shaft, a thermocouple, a dip tube and a cooling coil was charged in a drybox a mixture of (9-NMe-3)CrCl$_3$ (33 mg, 0.1 mmol), pentadecene (0.36 g, as internal reference for GC analysis), and toluene (100 ml). Into a 75 ml charging-bomb, which was connected to the dip tube of the Parr reactor at one end, was charged the above-prepared NHAO in toluene (7.53 g solution, 8.0 mmol Al). After sealing, the charging-bomb-connected reactor was transferred out of the drybox, connected to an ethylene cylinder at the other end of the charging-bomb, and heated to 105° C. Catalyst component mixing was carried out by pressing the NHAO solution in the charging-bomb into the reactor using ethylene gas, and in the meantime, the reactor was pressurized. The ethylene oligomerization reaction proceeded immediately at 105° C. under 425 psig ethylene pressure and was continued for 30 minutes with constant ethylene feeding to maintain the pressure. The reaction was then terminated by pressing an aqueous solution of potassium hydroxide into the reactor to deactivate the catalyst. Ethylene consumption was 32 grams as determined by weighing the ethylene cylinder. The reactor was then cooled to <10° C., vented and a sample was withdrawn for capillary GC analysis which showed a product distribution (weight percent) as follows: $C_4$: 9.4%, $C_6$: 39.3%, $C_8$: 10.0%, $C_{10}$: 8.5%, $C_{12}$: 6.9%, $C_{14}$: 6.0%, $C_{16}$: 5.0%, $C_{18}$: 4.0%, $C_{20+}$: 10.9%. The weight of $C_8$–$C_{18}$ fractions was used to calculate Schulz-Flory distribution coefficient $\beta$ (=0.41) by fitting the following simplified Schulz-Flory equation:

$$X_p = \beta/(1+\beta)^p$$

where $X_p$=mole fraction of $C_{2p+2}$ olefin

The weight of $C_4$ and $C_{20+}$ fractions was then obtained by extrapolation from Schulz-Flory distribution. The weight of $C_6$ fraction was calculated using measured response factor which was obtained from mimic experiments to simulate the operational loss. The selectivity of linear $\alpha$-olefin was 85–95% with major impurities being paraffins, internal olefins and cyclic olefins.

TABLE I

Ethylene Oligomerization/Trimerization/ Reactions Catalyzed by LCrX$_3$/Aluminoxane System

| EXAMPLE NO. | CATALYST[1] mmol | P psig | T °C. | SOLVENT[2] | TIME Min. | ACTIVITY mol/mol Cr/h[5] | $\beta^3$ | $C_6$ wt. %[4] Found | Calcd. |
|---|---|---|---|---|---|---|---|---|---|
| *Effects of Temperature and Pressure* | | | | | | | | | |
| 1 | (9-NMe-3)CrCl$_3$/NHAO(0.86) 0.067  5.8 | 815 | 130 | T | 30 | 18,214 | 0.8–1.1 | 46 | — |
| 2 | (9-NMe-3)CrCl$_3$/NHAO(0.86) 0.067  5.8 | 840 | 115 | T | 30 | 31,071 | 0.39 | 30 | 10 |
| 3 | (9-NMe-3)CrCl$_3$/NHAO(0.86) 0.05  4.0 | 540 | 115 | T | 30 | 21,429 | 0.56 | 46 | 12 |
| 4 | (9-NMe-3)CrCl$_3$/NHAO(0.86) 0.1  8.0 | 425 | 105 | T | 30 | 22,857 | 0.41 | 39 | 10 |
| 5 | (9-NMe-3)CrCl$_3$/NHAO(0.86) 0.067  6.0 | 230 | 95 | T | 30 | 17,143 | 0.30 | 37 | 6 |
| Comparison 1 | (9-NMe-3)CrCl$_3$/IBAO(0.88) 0.1  6.0 | 540 | 30 | CB | 30 | 1,948 | 0 (polymer only) | | |
| *Type of Aluminoxanes* | | | | | | | | | |
| 6 | (9-NMe-3)CrCl$_3$/IBAO(0.94) 0.1  10.0 | 440 | 105 | T | 30 | 8,571 | 0.40 | 40 | 9 |
| 7 | (9-NMe-3)CrCl$_3$/IBAO(0.94)/TNHA 0.1  8.0  2.0 | 440 | 105 | T | 30 | 18,571 | 0.42 | 36 | 10 |
| 8 | (9-NMe-3)CrCl$_3$/IBAO(0.94)/TEA 0.1  6.0  1.5 | 540 | 115 | CB | 30 | 7,929 | 0.44 | 36 | 9 |
| 9 | (9-NMe-3)CrCl$_3$/MAO(0.50) 0.1  6.0 | 550 | 115 | CB | 30 | 1,714 | 0.1–0.3 | 31 | — |
| *Effects of Solvent* | | | | | | | | | |
| 10 | (9-NMe-3)CrCl$_3$/IBAO(0.94)/TNHA 0.1  8.0  2.0 | 450 | 115 | CB | 30 | 8,571 | 0.49 | 44 | 11 |
| 11 | (9-NMe-3)CrCl$_3$/NHAO(0.86) 0.1  8.0 | 560 | 115 | H | 30 | 6,429 | 0.66 | 52 | 16 |
| 12 | (9-NMe-3)CrCl$_3$/NHAO(0.86) 0.067  5.8 | 820 | 115 | MCH | 30 | 20,256 | 0.50 | 35 | 12 |
| *Type of Chromium Compound* | | | | | | | | | |
| Comparison 2 | (9-NH-3)CrCl$_3$/NHAO(0.86) 0.1  10.0 | 430 | 105 | T | 5 | 69,231 | 0 (polymer only) | | |
| Comparison 3 | CrCl$_3$.3Py/NHAO(0.86) 0.1  8.0 | 420 | 105 | T | 30 | 12,143 | 0 (polymer only) | | |
| 13 | (9-NHMe-3)CrB$_3$/IBAO(0.94)/TEA 0.1  6.0  1.5 | 505 | 115 | CB | 30 | 3,571 | 0.2–0.4 | 26 | — |
| Comparison | (9-S-3)CrCl$_3$/IBAO(0.83) | 520 | 115 | CB | 60 | low (some polymer produced) | | | |

TABLE I-continued

Ethylene Oligomerization/Trimerization/ Reactions Catalyzed by LCrX₃/Aluminoxane System

| EXAMPLE NO. | CATALYST[1] mmol | | | P psig | T °C. | SOLVENT[2] | TIME Min. | ACTIVITY mol/mol Cr/h[5] | β[3] | C₆ wt. %[4] Found | Calcd. |
|---|---|---|---|---|---|---|---|---|---|---|---|
| 4 | 0.1 | 6.0 | | | | | | | | | |

Manner of Catalyst Component Mixing

| 14 | (9-NMe-3)CrCl₃/IBAO(0.94)/THNA | | | 430 | 115 | T | 50 | 3,857 | 0.69 | 43 | 12 |
| | 0.1 | 8.0 | 2.0 | | | | | | | | |
| 15 | (9-NMe-3)CrCl₃/NHAO(0.94)/THNA | | | 440 | 115 | T | 30 | 10,714 | 0.85 | 49 | 15 |
| | 0.1 | 8.0 | 2.0 | | | | | | | | |

[1]9-NMe-3 = 1,4,7-trimethyl-1,4,7-triazacyclononane, 9-NH-3 = 1,4,7-triazacyclononane. 9-S-3 = 1,4,7-trithiacyclononane. NHAO = n-hexylaluminoxane, IBAO = isobutylaluminoxane. The number in the parentheses represents the hydrolysis ratios. TEA = triethylaluminum, TNHA = tri-n-hexylaluminum. Py = pyridine
[2]T = toluene, CB = chlorobenzene, H = heptane, MCH = methylcyclohexane.
[3]β: Schulz-Flory distribution coefficient. Some reactions gave product distribution not following the Schulz-Flory rule. In those cases, a range of β was used to represent the product distribution between C₈ and C₁₈ (usually, β decreases as chain length becomes longer and, as a result, C₆ wt. % (calcd) could not be calculated.
[4]C₆ wt. % (found) = amount of C₆ found/ethylene consumption. C₆ wt. % (calcd) = amount of C₆ calculated from the Schuly Flory equation/ethylene consumption.
[5]Moles of ethylene per mole of chromium per hour.
For comparison with Example 15, Example 14 was carried out with a time lag of about 20 minutes between catalyst component mixing at room temperature (in the absence of ethylene) and ethylene reaction at 115° C.

Comparison 1 shows that for any given system at too low a temperature, only polymer results. Comparisons 2–4 show the need for alkyl substitution of the heteroatoms to provide an effective coordinating polydentate ligand in the chromium complex which provides oligomerization rather than polymerization. Oligomerization is believed to result from the difficult access of ethylene to the active catalyst sites which is afforded by such polydentate ligands. The amount of C₆ actually produced (trimerization) is, as shown by the last two columns in Table I, much greater than what is predicted by calculation. Also, the process of the invention favors the production of lower carbon number products compared to the prior art chain growth process on aluminum alkyls which provides products with a Poisson distribution of carbon numbers. When the prior art process is operated to peak the Poisson distribution at the lower carbon numbers (C₆–C₈) the products still include large amounts of the long chain olefin (C₁₀₊) and such products contain significant amounts of undesirable vinylidene isomers of such long chain olefins.

What is claimed is:

1. A process for preparing α-olefins, said process comprising oligomerizing ethylene in the presence of a catalyst comprising (a) a preformed chromium complex containing a coordinating polydentate ligand which inhibits ethylene polymerization and, (b) an aluminoxane, in an organic solvent so as to provide a chain growth product of C₄ to C₃₀ α-olefins having a Schultz-Flory distribution, which product is enriched in 1-hexene said polydentate ligand being a cyclic polyamine ligand represented by A—NR—B, where R is a C₁ to C₁₀ alkyl or a C₆ to C₂₀ aryl group, A represents the number of atoms in the ring and is an integer from 9 to 18 and B represents the number of nitrogen atoms in the ring and is an integer from 3 to 6, or a poly(pyrazolyl)borate anion of the type RB(P_z)₃ where R is a C₁ to C₁₀ alkyl group and P_z is a pyrazole or a substituted pyrazole.

2. The process of claim 1 wherein L is a cyclic polyamine ligand.

3. The process of claim 2 wherein said ligand is a 1,4,7-trialkyl-1,4,7-triazacyclononane.

4. The process of claim 3 wherein said ligand is 1,4,7-trimethyl-1,4,7-triazacyclononane.

5. The process of claim 1 wherein said complex is (1,4,7-trimethyl-1,4,7-triazacyclononane)CrCl₃.

6. The process of claim 1 wherein the oligomerization is conducted at a temperature of from about 35° to 200° C. and at an ethylene pressure of from about atmospheric to 3000 psig.

7. The process of claim 6 wherein the temperature is from about 95° to 150° C. and the ethylene pressure is from about 100 to 1500 psig.

8. The process of claim 1 wherein said aluminoxane contains alkyl groups having from 1 to about ten carbon atoms.

9. The process of claim 8 wherein said aluminoxane is selected from the group consisting of methylaluminoxane, isobutylaluminoxane and n-hexylaluminoxane, including mixtures thereof.

10. The process of claim 1 wherein said solvent is selected from hydrocarbons and halogenated hydrocarbons including mixtures thereof.

11. The process of claim 1 wherein the ratio of aluminum to chromium in the catalyst is from about 1:1 to about 10,000 to 1.

12. The process of claim 4, wherein the oligomerization is conducted at a temperature from about 95° to 150° C., an ethylene pressure of from about 100 to 1500 psig, and the ratio of aluminum to chromium in the catalyst is from about 5:1 to 500:1.

13. The process of claim 12 wherein the aluminoxane is n-hexylaluminoxane.

14. The process of claim 1 wherein the catalyst if formed by combining the chromium complex and the aluminoxane in an ethylene atmosphere.

15. The process of claim 12 wherein the catalyst is formed in situ by combining the chromium complex and the aluminoxane under ethylene pressure.

16. The process of claim 1 wherein the selectivity of linear α-olefin in said chain growth product is 85 to 95 weight percent with the major impurities being paraffins, internal olefins and cyclic olefins such that said chain growth product does not contain significant amounts of vinylidenes or polyethylene.

* * * * *

UNITED STATES PATENT AND TRADEMARK OFFICE
CERTIFICATE OF CORRECTION

PATENT NO. : 5,744,677
DATED : April 28, 1998
INVENTOR(S) : Feng-Jung Wu

It is certified that error appears in the above-identified patent and that said Letters Patent is hereby corrected as shown below:

| Col. | Line | |
|---|---|---|
| 5 | | (Table I, Example 13, Catalyst) reads "(9-NHMe-3)" should read --(9-NMe-3)-- |
| 7 | | (Table I, Example 14, Catalyst) reads "THNA" should read --TNHA-- |
| 7 | | (Table I, Example 15, Catalyst) reads "THNA" should read --TNHA-- |
| 8 | 55 | reads "the catalyst if formed" should read --the catalyst is formed-- |

Signed and Sealed this

Tenth Day of November 1998

Attest:

BRUCE LEHMAN

*Attesting Officer*   *Commissioner of Patents and Trademarks*